US00RE34661E

United States Patent [19]

Grim

[11] E Patent Number: Re. 34,661

[45] Reissued Date of Patent: Jul. 12, 1994

[54] GEL AND AIR CUSHION ANKLE BRACE

[75] Inventor: Tracy E. Grim, Broken Arrow, Okla.

[73] Assignee: Royce Medical Company, Westlake Village, Calif.

[21] Appl. No.: 935,013

[22] Filed: Aug. 25, 1992

Related U.S. Patent Documents

Reissue of:

[64] Patent No.: 5,088,478
Issued: Feb. 18, 1992
Appl. No.: 572,843
Filed: Aug. 24, 1990

U.S. Applications:

[63] Continuation-in-part of Ser. No. 308,689, Feb. 8, 1989, abandoned, which is a continuation-in-part of Ser. No. 192,461, May 10, 1988, Pat. No. 4,869,207.

[51] Int. Cl.[5] ..... A61F 5/00

[52] U.S. Cl. ..... 602/27; 128/DIG. 20; 602/13; 607/144; 607/96; 607/111

[58] Field of Search ..... 602/5, 13, 23, 27; 128/382, 399, 402, 594, 379, DIG. 20

[56] References Cited

U.S. PATENT DOCUMENTS 3,901,225 8/1975 Sconce .
4,411,077 10/1983 Slavitt .
4,495,942 1/1985 Palumbo .
4,502,470 3/1985 Kiser et al. ..... 128/DIG. 20 X
4,628,945 12/1986 Johnson, Jr. .
4,844,094 7/1989 Grim .
4,869,267 9/1989 Grim et al. .
4,964,402 10/1990 Grim et al. .
4,993,409 2/1991 Grim .

*Primary Examiner*—Richard J. Apley
*Assistant Examiner*—Linda C. M. Dvorak
*Attorney, Agent, or Firm*—Poms, Smith, Lande & Rose

[57] ABSTRACT

An ankle brace designed to be worn under the shoe has a first bladder which is filled with the high viscosity gel resistant to rapid deformation to apply pressure to the ankle and conform to its shape to provide support to the ankle. A second bladder inflatable with air is juxtaposed the first bladder to provide a uniform compressive force upon the bladder filled with the gel. A canvas ankle brace holds a pair of air and gel bladders along each of its sidewalls and is wrapped about the lower extremity and snugly fit thereto. Once the brace is in position, air is introduced into the second bladder to press the first bladder against the ankle and to conform to the shape thereof. Broad elastic straps may be secured to the lower rear of the brace to extend over the front of the ankle and the instep in a cruciate configuration. The outer ends of the straps are secured to lines which extend through openings in the outer casing of the brace, and D-rings secured to the ends of the lines permit the tensioning of the elastic straps by threading shoe laces through the rings and tightening the laces.

30 Claims, 4 Drawing Sheets

GEL AND AIR CUSHION ANKLE BRACE

Matter enclosed in heavy brackets [ ] appears in the original patent but forms no part of this reissue specification; matter printed in italics indicates the additions made by reissue.

RELATED PATENT APPLICATION

This is a Continuation-in-Part of U.S. patent application Ser. No. 308,689, filed Feb. 8, 1989, abandoned and U.S. patent application Ser. No. 192,461, filed May 10, 1988, now U.S. Pat. No. 4,869,207, granted Sept. 26, 1989.

FIELD OF THE INVENTION

The present invention relates generally to orthopedic devices and more particularly to a novel ankle brace having twin bladders, one bladder containing an orthopedic gel and the other bladder being inflatable to press the gel containing bladder against the ankle.

BACKGROUND OF THE INVENTION

Ankle braces are generally used to apply pressure to the ankle to prevent movement thereof after sustaining an injury. A constraint upon the application of such pressure is that it must generally restrict inversion and eversion (lateral) movement of the ankle while allowing the normal walking flexion of the ankle to occur.

In prior art attempts to construct an ankle brace which performs in accordance with the above constraint, inflatable air bladders have been used for developing the required pressure. For example, described in U.S. Pat. No. 3,811,434 (the '434 patent) is an inflatable splint having a flexible inflatable body portion to one side of which is joined a panel of flexible sheet material. The panel forms an open-ended sleeve with the body portion to admit a limb or the like and to enable the splint to be positioned. After the splint is properly positioned, the body portion is inflated. FIG. 7 of the '434 patent illustrates the use of the above-describe splint as an ankle brace.

A limitation and disadvantage of the inflatable spirnt described in the 434 patent is that when used on an ankle brace as shown therein inversion and eversion of the ankle is not adequately restrained since the inflatable body portion is designed to apply pressure against the shin and top of the foot thereby causing a tightening of the sheet material. At the ankle, the sheet material would only exhibit a minimal compressive force or pressure on the ankle due to the lateral tension between the body portion and sheet material. The further disadvantage and limitation of the above described splint is that it would resist normal walking flexion, which is desirable to promote healing, as the inflatable body portion would tend to straighten itself causing extension of the ankle. Also, the inflatable body portion would not be capable of being worn under a shoe, since the shoe would likely prevent proper inflation of the body portion under the shoe.

Another prior art ankle brace is described in U.S. Pat. No. 4,280,489 (the '489 patent). The brace of the '489 patent has a generally U-shaped stirrup having a base portion and a pair of opposed sidewall portions. An air inflatable liner is attached to the interior of each side wall and is dimensioned to extend coextensively therewith. The sidewall portions snugly fit about the lower leg above the ankle. Inflation of each liner applies pressure to the ankle.

A disadvantage and limitation of the device described in the '489 patent is that the use of air or any gaseous medium to provide the pressure on the ankle does not adequately prevent inversion or eversion of the ankle. For example, a sudden localized pressure applied to the air inflated liner is not resisted. The liner will be locally compressed causing the air to migrate to another portion of the liner to equalize the air pressure on the inner surface of the liner. Therefore, the air inflatable liner may not adequately restrain a sudden inversion or eversion of the ankle but may cause the stirrup to shift in position under such sudden and localized forces.

High viscosity gels are known to be highly resistive to sudden localized forces. These gels have found useful applications in ski boots. For example, see U.S. Pat. No. 3,237,319. Generally, a bladder is attached to an interior wall of the ski boot, the wall of the ski boot necessarily being extremely rigid The gel may be introduced into the bladder before or after the foot is placed in the boot. The gel, when the boot is tightened, will cause momentary discomfort but will gradually flow to conform to the shape of the ankle giving a high degree of comfort and support. Since the wall of the ski boot is rigid, the bladder will remain conformed to the ankle. During skiing, forces which may normally cause sudden inversion or eversion of the ankle are resisted because the high viscosity of the gel and its resistance to rapid deformation.

Although gel filled bladders are relatively advantageous in restraining inversion and eversion of the ankle when used within a ski boot, there are many problems and difficulties which arise when such bladders are to be substituted for the air filled liners of the above described ankle braces. Since it is highly desirable that such ankle braces be worn under clothing and especially shoes, the ankle brace must be relatively thin and flexible as opposed to the rigid wall of the ski boot. Since the high viscosity gel will gradually conform to the shape by which it is constrained, the gel bladder, if used in the prior art ankle braces will assume a shape that equalizes pressure the gel exerts across the inner surface of the bladder. For example, a shoe may cause the gel to evacuate partially from the bladder between the shoe and the ankle. Generally, the slow migration of the gel may cause the bladder to assume a shape which no longer supports the ankle against sudden inversion or eversion.

Attention is also directed to G. W. Johnson U.S. Pat. No. 4,628,945 in which an inflatable bladder is filled with foam and forms padding within a pair of rigid plastic members. In this regard, it may be noted general)y that braces of the type shown in the Johnson 945 and '489 patents, with stiff outer plastic members, are intended for use with incomplete or stable fractures, in some cases after partial mending, and for serious sprains, such as Grade III sprains. In addition, the engagement provided by the air bladder padding, even with a foam filler, is not as stable as might be desired, and is not compatible with hot and/or cold therapy.

J. W. Sconce U.S. Pat. No. 3,901,225 is also of interest in showing a rectangular or trapezoidal assembly forming a cast for immobilizing a fracture, using various hot or cold materials, with no mention of gel. Air inflation for immobilization and for forcing ice water or the like into contact with the fractured limb is provided.

The Spence U.S. Pat. No. 3,548,420 is also noted as disclosing simple gel pad structures and indicating the possibility of using gel pads with a "Milwaukee Brace", without disclosing any applicable structural arrangements.

SUMMARY OF THE INVENTION

It is therefore a feature of the present invention to provide an ankle brace wherein a gel filled bladder restrains the ankle against inversion and eversion. It is a further feature of the present invention to provide such an ankle brace which is thin and flexible so that it may be worn under articles of clothing, or within an athletic shoe.

According to one embodiment the present invention, a high viscosity gel, resistant to rapid deformation, is contained in a first bladder dimensioned to conform generally to a selected body portion, such as an ankle. A second bladder is shaped commensurately with and juxtaposed with respect to the first bladder. The second bladder may be inflated with air. A thin flexible sleeve-type brace is provided to fit snugly about the body portion with the two bladders arranged so that the air bladder is intermediate the gel bladder and the sleeve.

In a further embodiment of the present invention, each bladder has a first wall and a second wall with the walls being sealingly affixed at their peripheral edge. One wall of the gel bladder is juxtaposed against one wall of the air bladder.

An important advantage of the present invention is that the compressive force on one of the walls of the gel bladder is provided by the air bladder. Since the internal pressure of the air bladder is equalized over the inner surface of the bladder walls, a uniform compressive force is applied to the gel bladder wall at the interface with the air bladder. The gel will then conform to the selected body part. Another advantage and feature of the present invention is that the gel containing bladder may be removed from the ankle brace. The removed bladder may then be heated or cooled and reattached to the ankle brace for hot or cold therapy.

The present invention, in an important aspect thereof, involves the development of a new structure involving a flexible outer casing, and both an air bladder and an inner resilient pad preferably a gel pad, for the practical handling of Grade I and Grade II sprains or similar injuries of the ankle.

Furthermore, in accordance with an additional aspect of the invention, the device is formed in a fairly thin construction, so that it may fit within the user's shoe. Tying in with this use in a shoe, wide elastic straps may be coupled to tensioning lines which extend through openings in the outer flexible casing, to rings, such as D-rings, so that the shoe laces may be looped through the D-rings, and may be employed to tighten the broad elastic straps to the desired extent.

It is further noted that, as contrasted with the rectangular, or trapezoidal configuration of the Sconce device, the illustrative ankle brace is structurally formed in a non-rectangular shape, conforming to the shape of the ankle and foot so that pressure and support may be localized as desired, while still permitting limited and controlled movement and use of the ankle, while the user is recovering from the sprain.

These and other objects, advantages and features of the present invention will become more apparent to those skilled in the art from a study of the following description when read in conjunction with the attached drawing and appended claims.

DESCRIPTION OF THE PREFERRED EMBODIMENT

Figure 1:
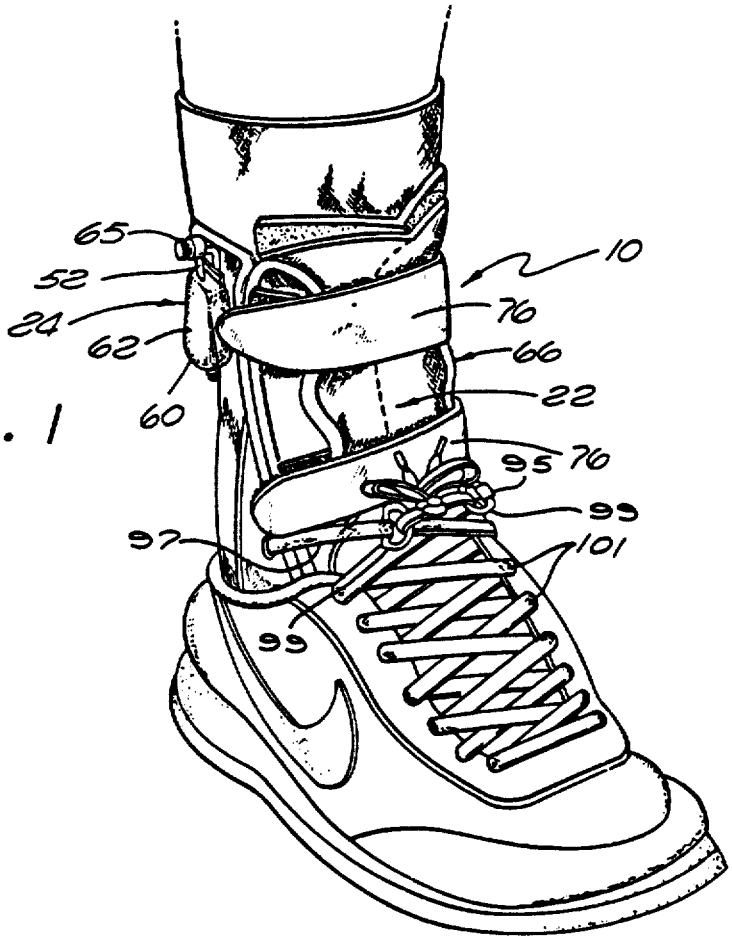
FIG. 1 illustrates an intended use of an ankle brace constructed according to the principles of the present invention.

Referring now to FIGS. 1-7, there is shown an orthopaedic device 10 for applying pressure to a selected body portion, exemplarily shown in FIG. 1 as an ankle. The orthopaedic device 10 includes a first bladder 12 having an interior chamber 14, a high viscosity gel or fluid 16 substantially filling the interior chamber 14 of the first bladder 12, a second bladder 18 having an interior chamber 20, means 22 for releasably securing the first bladder 12 adjacent the selected body portion, and means 24 for filling the interior chamber 20 of the second bladder 18 to apply compressive force upon the first bladder 12. The first bladder 12 applies pressure to the selected body portion in- response to the compressive force. Accordingly, the first bladder 12 is dimensioned conform to said selected body portion. The high viscosity gel 16 is selected to resist instantaneous forces incident upon said first bladder 12 yet it gradually forms about the selected body portion. For example, the gel may be sold under the brand name Elasto Gel, commercially available from Technologies Inc. of Kansas City, Mo. Also, the above referenced Pat. No. 3,237,319 discloses a variety of high viscosity materials which may be useful in practicing the present invention. As best seen FIG. 3 and 6, the second bladder 18 is juxtaposed with respect to the first bladder 12.

Figure 6:
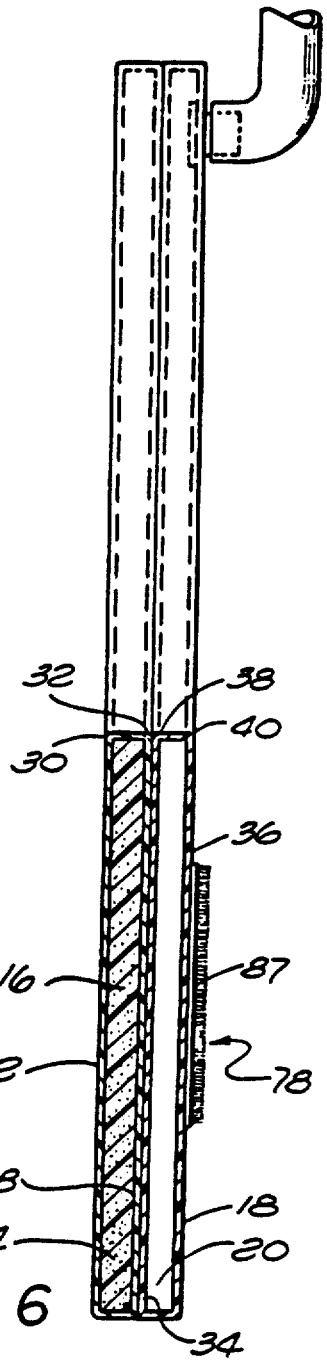
FIG. 6 is an enlarged cross-sectional view taken along line 6—6 of FIG. 5.

With particular reference to FIG. 6, the first bladder 12 has a first wall 26 and a second wall 28, the first wall 26 having a peripheral edge 30 and the second wall 28 having a peripheral edge 32. The peripheral edge 30 of the first wall 26 is sealingly affixed to the peripheral edge 32 of the second wall 28. For example, in one embodiment of the present invention, each of the first wall 26 and the second wall 28 may be formed from vinyl with their respective peripheral edges 30, 32 being conventionally sealed. Radio frequency (RF) sealing is one exemplary technique with which the peripheral edges 30, 32 of the first wall 26 and second wall 28 may be sealed together.

Figure 8:
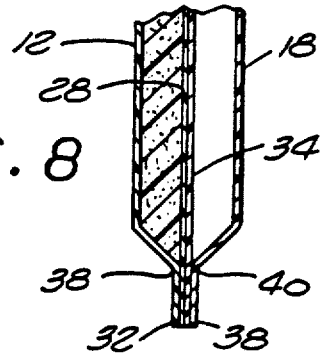
FIG. 8 shows an alternative configuration of one part of the ankle brace.

Similarly, the second bladder 18 includes a first wall 34 and a second wall 36. The first wall 34 having a peripheral edge 38 and a second wall 36 having a peripheral edge 40. As described hereinabove, the peripheral edge 38, 40 for each of the first wall 34 and second wall 36 of the second bladder 18 are conventionally sealed. The interior chamber 20 of the second bladder may be, in one embodiment of the present invention, filled with an air permeable foam (not shown). Alternatively, a single sheet of vinyl may form both the second wall 28 and first wall 34 with the respective edges being RF sealed as best seen in FIG. 8.

Figure 5:
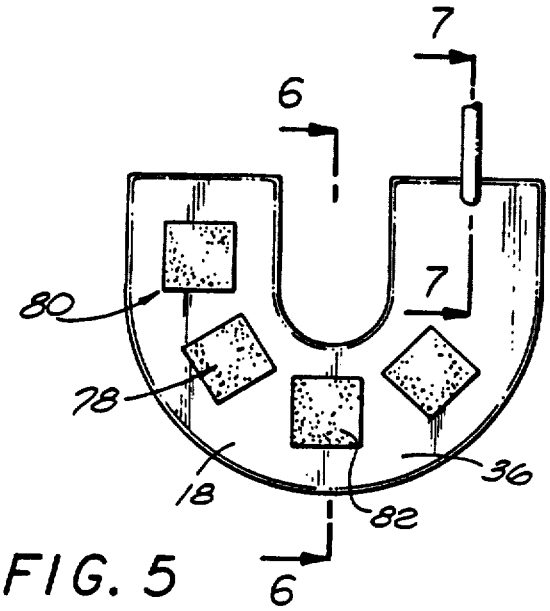
FIG. 5 is an elevational view of a portion of the ankle brace shown in FIG. 3.

With particular reference to FIG. 5, each of the first bladder 12 and the second bladder 18 are generally U-shaped. The second bladder 18 is also dimensioned conventionally with the first bladder 12. As best seen in FIG. 6, the second wall 28 of the first bladder 12 and the first wall 34 of the second bladder 18 are in a facing relationship to each other. The second wall 28 of the first bladder 12 and the first wall 34 of the second bladder 18 may either be permanently affixed or releasably attached to each other, by Velcro pads or other suitable means. For example, it may be desirable to remove the first bladder to heat the gel 16 prior to use of the orthopedic device 10.

Figure 4:
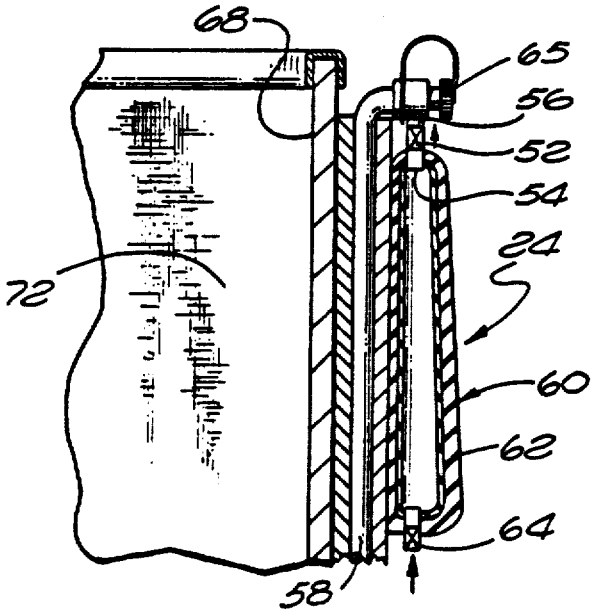
FIG. 4 is an enlarged view , a portion of the ankle brace in FIG. 3 as indicated by the oval designated 4 in FIG. 3.
Figure 7:
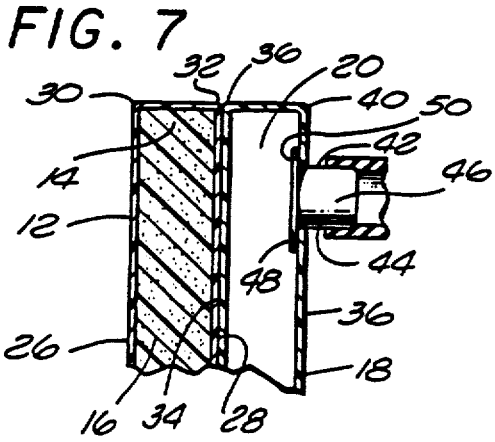
FIG. 7 is an enlarged cross-sectional view taken along line 7—7 of FIG. 5.

With particular reference to FIGS. 4 and 7, inflating means 24 includes a grommet 42 received through an opening 44 in the second wall 36 of the second bladder 18. Grommet 42 accordingly has a tubular portion 46 and an annular flange 48 affixed to an inner surface 50 of the second wall 36.

Inflating means 24 further includes a one-way air valve 52 having an inlet 54 and an outlet 56, a tube 58 operatively attached between the grommet 42 and the outlet 56. The tube 58 is releasably fitted to the grommet 42 after being slidably received over the tubular portion 46.

Inflating means 24 further includes an air pump 60 operatively coupled to the inlet 54 of the one-way air valve 52. Air pump 60 includes a squeeze bulb 62 and a second one-way air valve 64. Squeezing of the bulb 62 evacuate air therein through the first one-way air valve 52 to inflate the second bladder 18. Conversely, releasing of the squeeze bulb 62 causes air to fill the bulb 62 through the second one-way air valve 64. A release plug 65 for releasing air pressure from the interior chamber of the second bladder 18 may also be provided.

Securing means 22 includes a flexible brace 66 adapted for being disposed about lower extremity of a body. The outer casing of the brace 66 may be formed of canvas or similar material which is flexible but not stretchable to any significant extent. The brace 66 includes a pair of opposed sidewall portions 68, each of the sidewall 68 having a rear edge 70 elastically coupled to each other, an inner surface 72 and an outer surface 74. Securing means 22 further includes means 76 for adjusting the fit of the sidewall portions 68 about the lower extremity and means 78 for releasably attaching a separate bladder assembly to each inner surface 72 of each of the sidewall portions 68, in areas where the straps 91 and 93 are not interposed, and directly to the straps 91 and 93 where the straps are located between the bladders and the outer casing. The outer casing of the brace 66, useful in practicing the present invention is disclosed in commonly owned co-pending patent application, Ser. No. 192,461, now U.S. Pat. No. 4,869,267, issued Sept. 26, 1984, commercially available from Surefit Orthopedics, known as the EXCEL Ankle Support System. In this regard, the front edges of the outer casing may be secured together by the straps 76 secured to the left front side of the casing, as shown in FIG. 1, passing through openings near the right front edge, and returning to overlap each strap and being secured thereto by matching Velcro pads, all as shown and discussed in U.S. Pat. No. 4,869,267.

As best seen in FIG. 5, attaching means 78 includes a mateable fastener 80 having it first mating member 82 and a second mating member 84. First mating member 82 is mounted on the second wall 36 of the second bladder 18 the second mating matter is mounted on the inner surface 72 of the sidewall portion 68. For example, the mateable fastener 80 may be any conventional fastener commercially available under the Velcro trademark.

Figure 2:
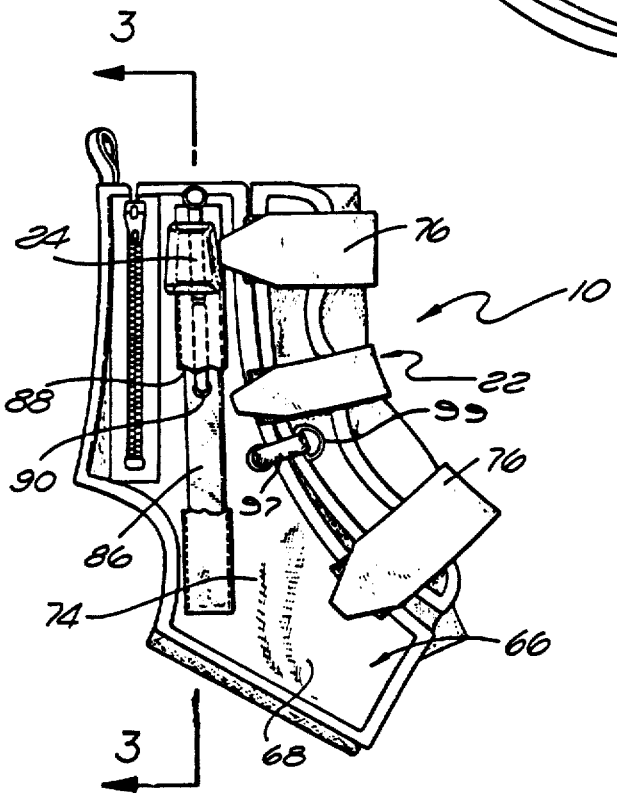
FIG. 2 is an elevational view of the ankle brace of FIG. 1.
Figure 3:
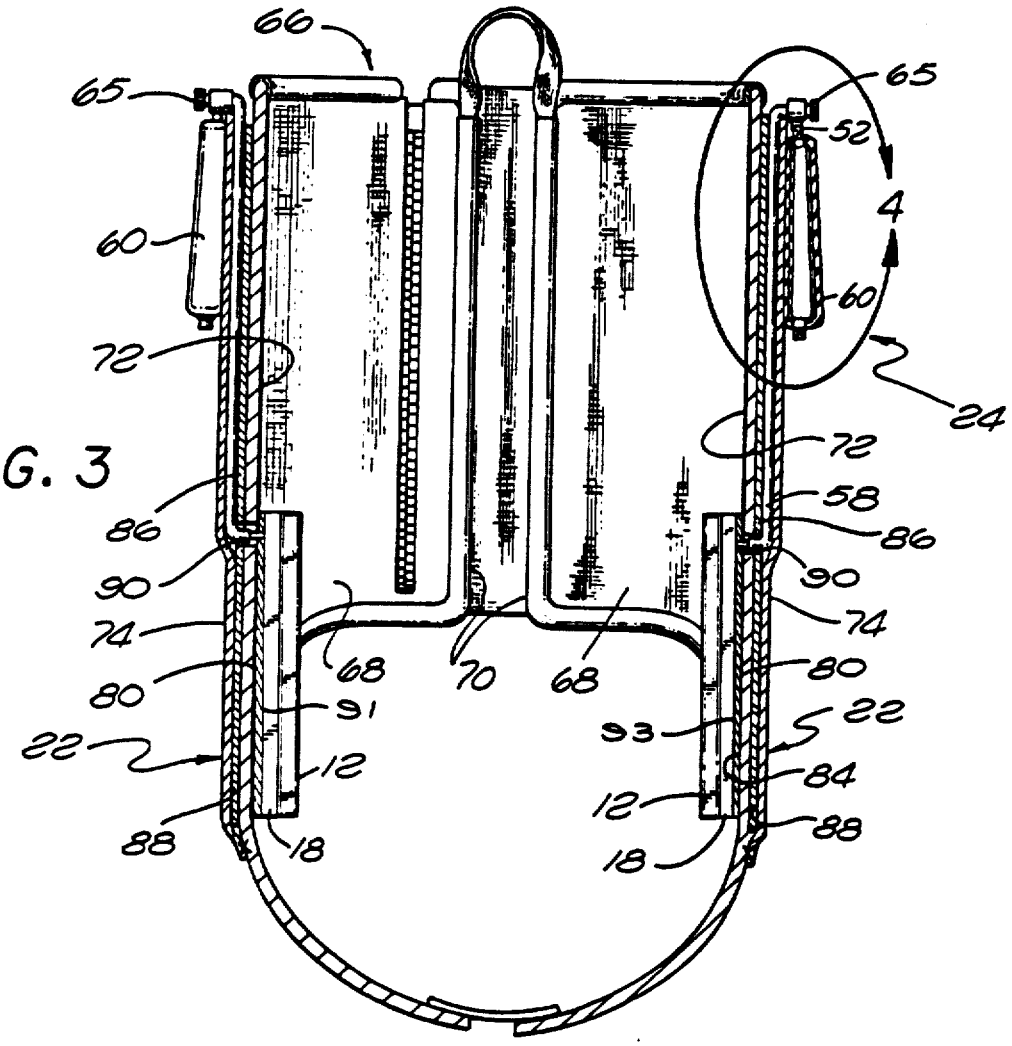
FIG. 3 is a cross-sectional view taken along line 3—3 of FIG. 2.

Each sidewall portions 68 includes a structural support 86 mounted on the outer surface 74 thereof. Structural support may be received by a pocket 88 sewn on to the outer surface 74 of each sidewall 68. The structural suppôrt of provides rigidity for carrying the inflating means 24. As best seen in FIGS. 2 and 3, the structural support 86 carries the tube 58 which is received through an opening 90.

Figure 9:
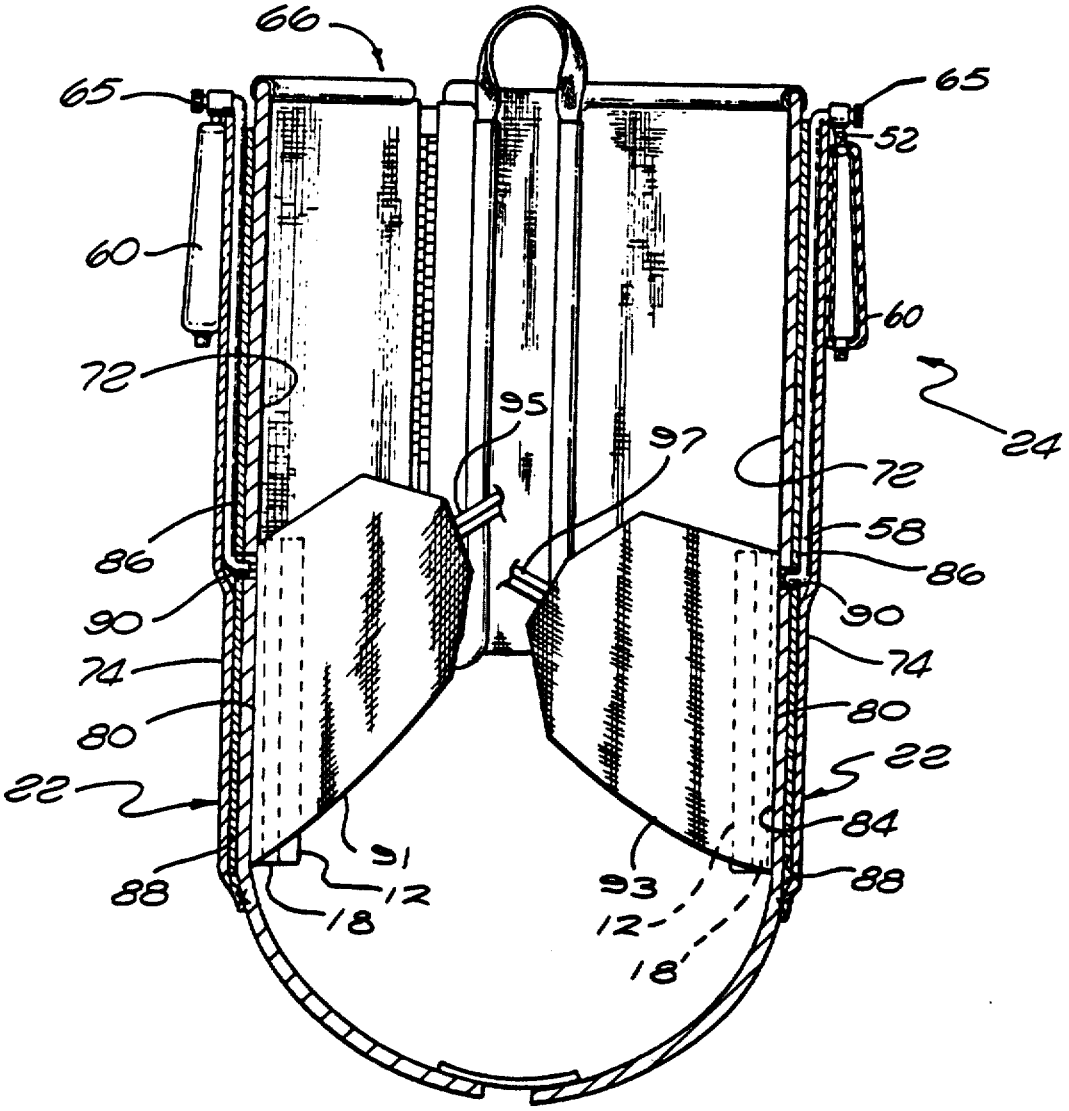
FIG. 9 is a view similar to FIG. 3, but showing the inner resilient strap arrangements.

Attention is now directed to FIG. 9 of the drawings which is a view similar to FIG. 3 of the drawings, but showing the broad, flexible elastic straps 91 and 93. These straps extend from the rear lower edge of the brace, and are secured to the outer casing at the rear lower edge at the opening for accommodating the user's heel (see FIG. 2). The straps 91 and 93 extend across one-another and overlap in a cruciate manner, and the lines 95 and 97, respectively, are secured to these straps. In FIG. 3, the elastic straps 91 and 93 are located between the air bladders 18 and the side walls 68 of the casing 66.

In FIGS. 1 and 2, the lines 95 and 97 are shown extending through openings in the outer casing of the brace 66, with D-rings 99 secured to the outer ends of lines 95 and 97. The laces 101 of the shoe are passed through the D-rings 99 and are tied together with tension to suit the needs of the user. By adjusting the tension applied to the cruciate straps and the inflation of the air bladders, appropriate support may be provided for the user, with the inner gel pads providing comfortable application of pressure or restraining force to the user's ankle. To facilitate putting the brace on, or taking it off, a zipper closure may be provided toward the rear of the brace, as shown in FIGS. 2 and 3.

There has been described hereinabove a novel orthopaedic device 10 which provides improved support for an ankle against inversion and eversion, while remaining small, compact, and light enough to be worn under an article of clothing, especially a shoe as seen in FIG. 1. It is further noted that in some cases the zipper at the rear of the casing may be omitted. Also, the orthopaedic assembly of the present invention could have the D-rings 99 secured directly to the outer flexible casing, or to a resilient or flexible strap extending around and secured to the rear of the casing, with the inner cruciate straps omitted, and with the air bladders and inner resilient pads mounted to the inner surfaces of the flexible casing. The front edges of the flexible casing may be held together by mating Velcro pads on the overlapping surfaces of the front edges, or by laces, instead of the use of straps as disclosed herein. From the foregoing examples, it is apparent that those skilled in the art may make numerous modifications of and departures from the above-described embodiments of the present invention as shown in the drawings and described hereinabove without departing from the inventive concepts described herein. Accordingly, the present invention is to be defined solely by the scope of the appended claims.

What is claimed is:

1. An ankle brace for use in connection with minor ankle injuries, such as Grade I or Grade II sprains, within a shoe, comprising:

an outer flexible casing conforming to the shape of the ankle and rear portion of the foot and having front edges which are close to one another along the front of the ankle and instep of the user;

means for adjustably holding said front edges together;

first and second wide elastic straps extending from said casing to cross over one-another in a cruciate configuration with one end of each of said straps being secured to said casing on different sides thereof;

first and second lines secured to the other ends of said first and second elastic straps, said lines extending through first and second holes, respectively, in said casing, on opposite sides thereof;

means secured to the outer ends of said lines for coupling to the laces of a shoe;

left and right air bladders mounted within said casing, on the sides thereof, and gel pad means mounted within said casing and within and adjacent said air bladders for cushioning the ankle and distributing inwardly directed pressure;

whereby the ankle of the user may be limited in its motion as desired by (1) varying the tightness of said casing, (2) varying the pressure in said air bladders, and (3) varying the tension applied from the shoe laces through said lines to said wide elastic straps.

2. A system including the brace as defined in claim 1 and further comprising a shoe having laces extending through rings secured to the outer ends of said lines, to apply tension to said straps.

3. An ankle brace as defined in claim 1 wherein said gel pad means and said air bladders are recessed to accommodate the malleolus.

4. An ankle brace as defined in claim 1 wherein said gel pad means and said air bladders are generally coextensive.

5. An ankle brace as defined in claim 1 further comprising valve means for retaining and/or releasing air from said air bladders.

6. An ankle brace as defined in claim 1 wherein said flexible casing is formed in two side sections secured together at the rear of the brace by elastic material.

7. An ankle brace for use in connection with minor ankle injuries such as Grade I or Grade II sprains, within a shoe, comprising:

an outer flexible casing conforming to the shape of the ankle and rear portion of the foot and having front edges which are close to one another along the front of the ankle and instep of the user; means for adjustably holding said front edges together;

first and second wide elastic straps extending from the lower rear of said casing to cross over oneanother in a cruciate configuration with one end of each of said straps being secured to said casing near the lower rear on different sides thereof;

first and second lines secured to the other ends of said first and second elastic straps, said lines extending through first and second holes, respectively in said casing, near opposite front edges thereof;

means secured to the outer ends of said lines for coupling to the laces of a shoe;

air bladder means mounted in said casing, on the sides thereof; and additional cushioning means mounted within said casing for cushioning the ankle;

whereby the ankle of the user may be limited in its motion as desired by (1) varying the tightness of said casing, (2) varying the pressure in said air bladders, and (3) varying the tension applied from the shoe laces through said lines to said broad elastic straps.

8. A system including the brace as defined in claim 7 and further comprising a shoe having laces extending through rings secured to the outer ends of said lines, to apply tension to said straps.

9. An ankle brace as defined in claim 7 wherein said air bladders are recessed to accommodate the malleolus.

10. An ankle brace as defined in claim 7 further comprising valve means for retaining and/or releasing air from said air bladders.

11. An ankle brace as defined in claim 7 wherein said flexible casing is formed in two side sections secured together at the rear of the brace by elastic material.

12. An ankle brace for insertion into a shoe for restraining and limiting motion of the ankle, comprising:

an outer flexible casing for mounting on the ankle, said casing opening at the front thereof and having opposed edges at each side of said opening;

pad members formed of a cushioning flexible material mounted within said casing adjacent the sides of the user's ankle;

air bladders mounted within said casing between said pad members and said casing;

means for securing the front edges of said casing together;

means for inflating said air bladders; and fastening means secured to said casing for receiving shoe laces so that the shoe laces may be tightened and tied, to couple the shoe to the ankle brace.

13. An ankle brace as defined in claim 12 wherein said brace includes broad elastic straps secured to said casing near the rear thereof on two sides thereof and extending across the front of the ankle in a cruciate configuration, and wherein said fastening means includes lines secured to said straps extending through openings in said casing, and rings secured on the outer ends of said lines, through which the shoe laces may be tied.

14. An ankle brace for applying pressure to an ankle to restrain inversion and eversion movement of said ankle comprising:

a first bladder having an interior chamber, said bladder being dimensioned to conform to said ankle;

gel type materials substantially filling said interior chamber, said material being selected to resist instantaneous forces applied to said first bladder and to form about said ankle;

a second bladder having an interior chamber, said second bladder being juxtaposed with respect to said first bladder;

means for inflating said interior chamber of said second bladder to apply compressive force upon said first bladder, said first bladder applying pressure to said ankle in response to said compressive force;

a flexible outer casing adapted for being disposed about said ankle, said casing including a first pair of opposed sidewall portions, each of said sidewall portions having a rear edge elastically coupled to each other, an inner surface and an outer surface;

means for adjusting the fit of said sidewall portions about said ankle; and means for releasably attaching said second bladder to said inner surface of each of said sidewall portions.

15. A brace for permitting limited or restricted movement of a portion of the human body which has been subject to minor injury, comprising:

an outer flexible casing conforming to the shape of the portion of the anatomy as to which limited movement is to be permitted;

means for adjustably holding said flexible casing to the body of the user;

at least one gel pad for mounting within said casing and adjacent the anatomy and for cushioning and conforming to the physical configuration of the anatomy of the user;

at least one air bladder mounted between the gel pad and the casing;

means for inflating said bladder to apply pressure to said gel pad to exert a restraining force to limit movement of the selected portion of the anatomy; and said brace further including resilient or elastic means for applying additional force to said gel pad in combination with that provided by said air bladder.

16. A brace as defined in claim 15 wherein two gel pads and two air bladders are provided, and means are provided for mounting one air bladder and one gel on either side of the ankle.

17. A brace as defined in claim 16 wherein said resilient or elastic means includes first and second broad elastic straps mounted within said casing to extend across the instep and/or the front of the ankle in a cruciate configuration.

18. A brace as defined in claim 17 further including means secured to said elastic straps for coupling to the laces of a shoe for tensioning said elastic straps.

19. A brace as defined in claim 15 further including means for adjusting the tension of said resilient or elastic means.

20. An ankle brace for use in connection with minor ankle injuries, such as Grade I or Grade II sprains, within a shoe, comprising:

an outer flexible casing conforming to the shape of the ankle and rear portion of the foot and having front edges which are close to one another along the front of the ankle and instep of the user;

means for adjustably holding said front edges together;

first and second wide elastic straps extending from said casing to cross over one-another in a cruciate configuration with one end of each of said straps being secured to said casing on different sides thereof;

first and second lines secured to the other ends of said first and second elastic straps, said lines extending through first and second holes, respectively, in said casing, on opposite sides thereof;

means secured to the outer ends of said lines for coupling to the laces of a shoe; and air bladder means mounted within said casing, on the sides thereof;

whereby the ankle of the user may be limited in its motion as desired by (1) varying the tightness of said casing, (2) varying the pressure in said air bladders, and (3) varying the tension applied from the shoe laces through said lines to said broad elastic straps.

21. A system including the brace as defined in claim 20 and further comprising a shoe having laces extending through rings secured to the outer ends of said lines, to apply tension to said straps.

22. An ankle brace as defined in claim 20 wherein said air bladders are recessed to accommodate the malleolus.

23. An ankle brace as defined in claim 20 wherein said flexible casing is formed in two side sections secured together at the rear of the brace by elastic material.

24. A brace for permitting limited or restricted movement of a portion of the human body which has been subject to minor injury, comprising:

an outer support member conforming to the shape of the portion of the anatomy as to which limited movement is to be permitted;

means for adjustably holding said support member to the body of the user;

at least one gel pad for mounting within said support member and adjacent the anatomy, and for cushioning and conforming to the physical configuration of the anatomy of the user;

at least one air bladder mounted adjacent said gel pad and within the support member; and means for inflating said bladder to apply pressure to the selected portion of the anatomy to exert a restraining force to limit movement of the selected portion of the anatomy;

whereby the gel permits full conformation to the anatomy and the use of an air bladder provides adjustable support.

25. A brace for permitting limited or restricted movement of a portion of the human body which has been subject to minor injury, comprising:

an outer support member conforming to the shape of the portion of the anatomy as to which limited movement is to be permitted;

means for adjustably holding said support member to the body of the user;

at least one gel pad for mounting within said support *member* and adjacent the anatomy and for cushioning and conforming to the physical configuration of the anatomy of the user;

at least one air bladder mounted between the gel pad and the support member; and means for inflating said bladder to apply pressure to said gel pad to exert a restraining force to limit movement of the selected portion of the anatomy;

whereby the gel permits full conformation to the anatomy and the use of an air bladder provides adjustable support.

26. An orthopaedic device comprising:

means for applying pressure to the user's ankle to restrain motion of the ankle while permitting limited movement thereof; said means including:

a first bladder having an interior chamber, said bladder being dimensioned to conform to the configuration of the ankle;

gel type material substantially filling said interior chamber, said material constituting means for resisting instantaneous forces applied to said first bladder and for conforming to the shape of the ankle;

a second bladder having an interior chamber, said second bladder being juxtaposed with respect to said first bladder;

means for releasably securing said first bladder adjacent the user's ankle; and means for inflating said interior chamber of said second bladder to apply a compressive force upon said first bladder, said first bladder applying pressure to the user's ankle portion in response to said compressive force; and means including a flexible casing for mounting on the user's ankle and for holding said bladders in engagement with the ankle, said flexible casing including a first section for engaging the lower part of a patient's leg, and a second portion extending at a substantial angle to said first portion for encircling and engaging the patient's foot and instep adjacent the ankle.

27. A device as set forth in claim 26 wherein said first bladder is generally U-shaped.

28. A device as defined in claim 26 wherein said first bladder is recessed to accommodate the malleolus.

*29. A brace for permitting limited or restricted movement of a portion of the human body which has been subject to minor injury, comprising:*

*an outer support member conforming to the shape of the portion of the anatomy as to which limited movement is to be permitted;*

*means for adjustably holding said support member to the body of the user;*

*at least one gel pad for mounting within said support member and adjacent the anatomy and for cushioning and conforming to the physical configuration of the anatomy of the user;*

*at least one air bladder mounted adjacent said gel pad and the support member; and*

*said bladder constituting means for containing air to apply pressure to the selected portion of the anatomy to exert a restraining force to limit movement of the selected portion of the anatomy;*

*whereby the gel permits full conformation to the anatomy and the use of an air bladder provides additional support.*

*30. A brace as defined in claim 29, in which the bladder is inflatable and is mounted between the gel pad and within the support member, whereby the gel provides adjustable support.*

* * * * *